United States Patent [19]

Murdock

[11] Patent Number: 5,374,543
[45] Date of Patent: Dec. 20, 1994

[54] ENHANCED INDOLE BIOSYNTHESIS

[75] Inventor: Douglas C. Murdock, Thousand Oaks, Calif.

[73] Assignee: Amgen Inc., Thousands Oaks, Calif.

[21] Appl. No.: 956,697

[22] Filed: Oct. 2, 1992

[51] Int. Cl.$^5$ .................. C12P 17/12; C12P 7/22; C12N 1/20; C07H 19/00

[52] U.S. Cl. .................. 435/122; 435/69.1; 435/71.1; 435/156; 435/172.3; 435/240.2; 435/252.3; 435/252.33; 435/252.34; 435/320.1; 536/22.1; 536/23.1; 536/23.2; 536/23.7

[58] Field of Search ............... 435/121, 122, 126, 128, 435/172.1, 172.3, 320.1, 69.1, 822, 848, 849, 911, 946, 947, 948, 252.3, 252.33, 171.1, 156, 240.2, 252.34; 536/27, 22.1, 23.1, 23.2, 23.7; 530/350

[56] References Cited

PUBLICATIONS

Bang et al. "Production of L-Tryptophan . . ." *Biotech & Bioengineering* vol. 25, pp. 999–1011, 1013–1025 (1983).
Yanofsky et al "The exclusion of free indole as . . ." *Biochim. Biophys. Acta.*, 28:640–641 (1958).
Yanofsky et al. "The effects of deletions, point mutations . . ." *P.N.A.S.*, 45:1016–1026 (1959).
Yanofsky et al. "The complete nucleotide sequence . . ." *Nucleic Acid Research*, 9:24, 6647–6667 (1981).
Hyde et al. "Three dimensional structure of the tryptophan . . ." *Journal of Biological Chemistry*, 263:33, 17857–17871 (1988).
Cotton et al. "Tryptophan synthetase $\beta_2$ subunit . . ." *Journal of Biological Chemistry*, 247:6, 1883–1891 (1972).
Ensley et al. "Expression of naphthalene oxidation . . ." *Science*, 222:167–169 (1983).
Kolter et al., *J. Mol. Biol.*, 175:299–312 (1984).
Roesser et al., *Journ. of Biol. Chemistry*, 263:28, 14252–14255 (1988).
Das et al., *Nucleic Acids Research*, 12:11, 4757–4768 (1984).
Enger-Valk et al., *Gene*, 9:69–85 (1980).
Stewart et al., *Journal of Bacteriology*, 167:1, 383–386 (1986).
Hyde et al., *Biotechnology*, 8:27–32 (1990).
Yanofsky, C., *Biochimica Biophysica Acta*, 1000:133–137 (1989).
Ahmed et al., *Biochemistry*, 25:3118–3124 (1986).
Djavadi-Ohaniance et al., *Biochemistry*, 25:2502–2508 (1986).
Miles et al., *Journal of Biological Chemistry*, 264:11, 6280–6287 (1989).
Nagata et al., *Journal of Biological Chemistry*, 264:11, 6288–6296 (1989).
Ahmed et al., *Biochemical and Biophysical Research Communications*, 151:2, 672–678 (1988).
Crawford et al., *Ann. Rev. Biochem.*, 49:163–195 (1980).
Yanofsky, C., *Nature*, 289:751–758 (1981).
Kolter et al., *Ann. Rev. Genet.*, 16:113–134 (1982).
Landick et al., *Journal of Biological Chemistry*, 259:18, 11550–11555 (1984).
Dekel-Gorodetsky et al., *Journal of Bacteriology*, 165:3, 1046–1048 (1986).
Aiba et al., *Applied and Environmental Microbiology*, 43:2, 289–297 (1982).
Tribe et al., *Applied and Environmental Microbiology*, 38:2, 181–190 (1979).

*Primary Examiner*—Robert A. Wax
*Assistant Examiner*—Hyosuk Kim
*Attorney, Agent, or Firm*—Daniel M. Chambers; Ron K. Levy; Steven M. Odre

[57] ABSTRACT

DNA molecules encoding a modified tryptophan synthase beta subunit are disclosed. When expressed in a recombinant host microorganism, these polypeptide analogs enable significant levels of intracellular indole production and accumulation. In the presence of an aromatic dioxygenase enzyme, the indole so produced can be converted to indoxyl, which upon exposure to air oxidizes to indigo.

22 Claims, 3 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
  ( A ) LENGTH: 12 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1:

CATCGATTCT AG                      12

( 2 ) INFORMATION FOR SEQ ID NO:2:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2:

AATTCTAGAA TCGATGACGT                 20

( 2 ) INFORMATION FOR SEQ ID NO:3:

( i ) SEQUENCE CHARACTERISTICS:
  ( A ) LENGTH: 36 base pairs
  ( B ) TYPE: nucleic acid
  ( C ) STRANDEDNESS: double
  ( D ) TOPOLOGY: unknown ( x i ) SEQUENCE DESCRIPTION: SEQ ID NO:3:

```
GTT  AAC  CTT  TCC  GGT  CGC  GGC  GAT  AAA  GAC  ATC  TTC         36
Val  Asn  Leu  Ser  Gly  Arg  Gly  Asp  Lys  Asp  Ile  Phe
 1              5                        10
```

( 2 ) INFORMATION FOR SEQ ID NO:4:

( i ) SEQUENCE CHARACTERISTICS:
  ( A ) LENGTH: 1193 base pairs
  ( B ) TYPE: nucleic acid
  ( C ) STRANDEDNESS: unknown
  ( D ) TOPOLOGY: unknown ( x i ) SEQUENCE DESCRIPTION: SEQ ID NO:4:

```
ATG  ACA  ACA  TTA  CTT  AAC  CCC  TAT  TTT  GGT  GAG  TTT  GGC  GGC  ATG  TAC       48
Met  Thr  Thr  Leu  Leu  Asn  Pro  Tyr  Phe  Gly  Glu  Phe  Gly  Gly  Met  Tyr
 1                   5                        10                       15

GTG  CCA  CAA  ATC  CTG  ATG  CCT  GCT  CTG  CGC  CAG  CTG  GAA  GAA  GCT  TTT       96
Val  Pro  Gln  Ile  Leu  Met  Pro  Ala  Leu  Arg  Gln  Leu  Glu  Glu  Ala  Phe
                     20                       25                       30

GTC  AGT  GCG  CAA  AAA  GAT  CCT  GAA  TTT  CAG  GCT  CAG  TTC  AAC  GAC  CTG      144
Val  Ser  Ala  Gln  Lys  Asp  Pro  Glu  Phe  Gln  Ala  Gln  Phe  Asn  Asp  Leu
           35                       40                       45

CTG  AAA  AAC  TAT  GCC  GGG  CGT  CCA  ACC  GCG  CTG  ACC  AAA  TGC  CAG  AAC      192
Leu  Lys  Asn  Tyr  Ala  Gly  Arg  Pro  Thr  Ala  Leu  Thr  Lys  Cys  Gln  Asn
     50                       55                       60

ATT  ACA  GCC  GGG  ACG  AAC  ACC  ACG  CTG  TAT  CTC  AAG  CGT  GAA  GAT  TTG      240
Ile  Thr  Ala  Gly  Thr  Asn  Thr  Thr  Leu  Tyr  Leu  Lys  Arg  Glu  Asp  Leu
 65                       70                       75                       80

CTG  CAC  GGC  GGC  GCG  CAT  AAA  ACT  AAC  CAG  GTG  CTG  GGG  CAG  GCG  TTG      288
Leu  His  Gly  Gly  Ala  His  Lys  Thr  Asn  Gln  Val  Leu  Gly  Gln  Ala  Leu
                     85                       90                       95

CTG  GCG  AAG  CGG  ATG  GGT  AAA  ACC  GAA  ATC  ATC  GCC  GAA  ACC  GGT  GCC      336
Leu  Ala  Lys  Arg  Met  Gly  Lys  Thr  Glu  Ile  Ile  Ala  Glu  Thr  Gly  Ala
                100                      105                      110

GGT  CAG  CAT  GGC  GTG  GCG  TCG  GCC  CTG  GCC  AGC  GCC  CTG  CTC  GGC  CTG      384
Gly  Gln  His  Gly  Val  Ala  Ser  Ala  Leu  Ala  Ser  Ala  Leu  Leu  Gly  Leu
           115                      120                      125
```

-continued

| | | | | | | | | | | | | | | | | |
|---|---|---|---|---|---|---|---|---|---|---|---|---|---|---|---|---|
| AAA | TGC | CGT | ATT | TAT | ATG | GGT | GCC | AAA | GAC | GTT | GAA | CGC | CAG | TCG | CCT | 432 |
| Lys | Cys | Arg | Ile | Tyr | Met | Gly | Ala | Lys | Asp | Val | Glu | Arg | Gln | Ser | Pro | |
| 130 | | | | | 135 | | | | | 140 | | | | | | |
| AAC | GTT | TTT | CGT | ATG | CGC | TTA | ATG | GGT | GCG | GAA | GTG | ATC | CCG | GTG | CAT | 480 |
| Asn | Val | Phe | Arg | Met | Arg | Leu | Met | Gly | Ala | Glu | Val | Ile | Pro | Val | His | |
| 145 | | | | | 150 | | | | | 155 | | | | | 160 | |
| AGC | GGT | TCC | GCG | ACG | CTG | AAA | GAT | GCC | TGT | AAC | GAG | GCG | CTG | CGC | GAC | 528 |
| Ser | Gly | Ser | Ala | Thr | Leu | Lys | Asp | Ala | Cys | Asn | Glu | Ala | Leu | Arg | Asp | |
| | | | | 165 | | | | | 170 | | | | | 175 | | |
| TGG | TCC | GGT | AGT | TAC | GAA | ACC | GCG | CAC | TAT | ATG | CTG | GGC | ACC | GCA | GCT | 576 |
| Trp | Ser | Gly | Ser | Tyr | Glu | Thr | Ala | His | Tyr | Met | Leu | Gly | Thr | Ala | Ala | |
| | | | 180 | | | | | 185 | | | | | 190 | | | |
| GGC | CCG | CAT | CCT | TAT | CCG | ACC | ATT | GTG | CGT | GAG | TTT | CAG | CGG | ATG | ATT | 624 |
| Gly | Pro | His | Pro | Tyr | Pro | Thr | Ile | Val | Arg | Glu | Phe | Gln | Arg | Met | Ile | |
| | | 195 | | | | | 200 | | | | | 205 | | | | |
| GGC | GAA | GAA | ACC | AAA | GCG | CAG | ATT | CTG | GAA | AGA | GAA | GGT | CGC | CTG | CCG | 672 |
| Gly | Glu | Glu | Thr | Lys | Ala | Gln | Ile | Leu | Glu | Arg | Glu | Gly | Arg | Leu | Pro | |
| 210 | | | | | 215 | | | | | 220 | | | | | | |
| GAT | GCC | GTT | ATC | GCC | TGT | GTT | GGC | GGC | GGT | TCG | AAT | GCC | ATC | GGC | ATG | 720 |
| Asp | Ala | Val | Ile | Ala | Cys | Val | Gly | Gly | Gly | Ser | Asn | Ala | Ile | Gly | Met | |
| 225 | | | | | 230 | | | | | 235 | | | | | 240 | |
| TTT | GCT | GAT | TTC | ATC | AAT | GAA | ACC | AAC | GTC | GGC | CTG | ATT | GGT | GTG | GAG | 768 |
| Phe | Ala | Asp | Phe | Ile | Asn | Glu | Thr | Asn | Val | Gly | Leu | Ile | Gly | Val | Glu | |
| | | | | 245 | | | | | 250 | | | | | 255 | | |
| CCA | GGT | GGT | CAC | GGT | ATC | GAA | ACT | GGC | GAG | CAC | GGC | GCA | CCG | CTA | AAA | 816 |
| Pro | Gly | Gly | His | Gly | Ile | Glu | Thr | Gly | Glu | His | Gly | Ala | Pro | Leu | Lys | |
| | | | 260 | | | | | 265 | | | | | 270 | | | |
| CAT | GGT | GCG | GTG | GGT | ATC | TAT | TTC | GGT | ATG | AAA | GCG | CCG | ATG | ATG | CAA | 864 |
| His | Gly | Ala | Val | Gly | Ile | Tyr | Phe | Gly | Met | Lys | Ala | Pro | Met | Met | Gln | |
| | | 275 | | | | | 280 | | | | | 285 | | | | |
| ACC | GAA | GAC | GGG | CAG | ATT | GAA | GAA | TCT | TAC | TCC | ATC | TCC | GCC | GGA | CTG | 912 |
| Thr | Glu | Asp | Gly | Gln | Ile | Glu | Glu | Ser | Tyr | Ser | Ile | Ser | Ala | Gly | Leu | |
| 290 | | | | | 295 | | | | | 300 | | | | | | |
| GAT | TTC | CCG | TCT | GTC | GGC | CCA | CAA | CAC | GCG | TAT | CTT | AAC | AGC | ACT | GGA | 960 |
| Asp | Phe | Pro | Ser | Val | Gly | Pro | Gln | His | Ala | Tyr | Leu | Asn | Ser | Thr | Gly | |
| 305 | | | | | 310 | | | | | 315 | | | | | 320 | |
| CGC | GCT | GAT | TAC | GTG | TCT | ATT | ACC | GAT | GAT | GAA | GCC | CTT | GAA | GCC | TTC | 1008 |
| Arg | Ala | Asp | Tyr | Val | Ser | Ile | Thr | Asp | Asp | Glu | Ala | Leu | Glu | Ala | Phe | |
| | | | | 325 | | | | | 330 | | | | | 335 | | |
| AAA | ACG | CTG | TGC | CTG | CAC | GAA | GGG | ATC | ATC | CCG | GCG | CTG | GAA | TCC | TCC | 1056 |
| Lys | Thr | Leu | Cys | Leu | His | Glu | Gly | Ile | Ile | Pro | Ala | Leu | Glu | Ser | Ser | |
| | | | 340 | | | | | 345 | | | | | 350 | | | |
| CAC | GCC | TTG | GCC | CAT | GCG | TTG | AAA | ATG | ATG | CGC | GAA | AAC | CCG | GAT | AAA | 1104 |
| His | Ala | Leu | Ala | His | Ala | Leu | Lys | Met | Met | Arg | Glu | Asn | Pro | Asp | Lys | |
| | | 355 | | | | | 360 | | | | | 365 | | | | |
| GAG | CAG | CTA | CTG | GTG | GTT | AAC | CTT | TCC | GGT | CGC | GGC | GAT | AAA | GAC | ATC | 1152 |
| Glu | Gln | Leu | Leu | Val | Val | Asn | Leu | Ser | Gly | Arg | Gly | Asp | Lys | Asp | Ile | |
| | 370 | | | | | 375 | | | | | 380 | | | | | |
| TTC | ACC | GTT | CAC | GAT | ATT | TTG | AAA | GCA | CGA | GGG | GAA | ATC | TG | | | 1193 |
| Phe | Thr | Val | His | Asp | Ile | Leu | Lys | Ala | Arg | Gly | Glu | Ile | | | | |
| 385 | | | | 390 | | | | | 395 | | | | | | | |

( 2 ) INFORMATION FOR SEQ ID NO:5:

( i ) SEQUENCE CHARACTERISTICS:
        ( A ) LENGTH: 397 amino acids
        ( B ) TYPE: amino acid
        ( D ) TOPOLOGY: linear ( x i ) SEQUENCE DESCRIPTION: SEQ ID NO:5:

| | | | | | | | | | | | | | | |
|---|---|---|---|---|---|---|---|---|---|---|---|---|---|---|
| Met | Thr | Thr | Leu | Leu | Asn | Pro | Tyr | Phe | Gly | Glu | Phe | Gly | Gly | Met | Tyr |
| 1 | | | | 5 | | | | | 10 | | | | | 15 | |
| Val | Pro | Gln | Ile | Leu | Met | Pro | Ala | Leu | Arg | Gln | Leu | Glu | Glu | Ala | Phe |

-continued

| | | 20 | | | | 25 | | | | 30 | | | |
|---|---|---|---|---|---|---|---|---|---|---|---|---|---|
| Val | Ser | Ala | Gln | Lys | Asp | Pro | Glu | Phe | Gln | Ala | Gln | Phe | Asn | Asp | Leu |
| | | 35 | | | | | 40 | | | | | 45 | | | |
| Leu | Lys | Asn | Tyr | Ala | Gly | Arg | Pro | Thr | Ala | Leu | Thr | Lys | Cys | Gln | Asn |
| | 50 | | | | | 55 | | | | | 60 | | | | |
| Ile | Thr | Ala | Gly | Thr | Asn | Thr | Thr | Leu | Tyr | Leu | Lys | Arg | Glu | Asp | Leu |
| 65 | | | | | 70 | | | | | 75 | | | | | 80 |
| Leu | His | Gly | Gly | Ala | His | Lys | Thr | Asn | Gln | Val | Leu | Gly | Gln | Ala | Leu |
| | | | | 85 | | | | | 90 | | | | | 95 | |
| Leu | Ala | Lys | Arg | Met | Gly | Lys | Thr | Glu | Ile | Ile | Ala | Glu | Thr | Gly | Ala |
| | | | 100 | | | | | 105 | | | | | 110 | | |
| Gly | Gln | His | Gly | Val | Ala | Ser | Ala | Leu | Ala | Ser | Ala | Leu | Leu | Gly | Leu |
| | | 115 | | | | | 120 | | | | | 125 | | | |
| Lys | Cys | Arg | Ile | Tyr | Met | Gly | Ala | Lys | Asp | Val | Glu | Arg | Gln | Ser | Pro |
| | 130 | | | | | 135 | | | | | 140 | | | | |
| Asn | Val | Phe | Arg | Met | Arg | Leu | Met | Gly | Ala | Glu | Val | Ile | Pro | Val | His |
| 145 | | | | | 150 | | | | | 155 | | | | | 160 |
| Ser | Gly | Ser | Ala | Thr | Leu | Lys | Asp | Ala | Cys | Asn | Glu | Ala | Leu | Arg | Asp |
| | | | | 165 | | | | | 170 | | | | | 175 | |
| Trp | Ser | Gly | Ser | Tyr | Glu | Thr | Ala | His | Tyr | Met | Leu | Gly | Thr | Ala | Ala |
| | | | 180 | | | | | 185 | | | | | 190 | | |
| Gly | Pro | His | Pro | Tyr | Pro | Thr | Ile | Val | Arg | Glu | Phe | Gln | Arg | Met | Ile |
| | | 195 | | | | | 200 | | | | | 205 | | | |
| Gly | Glu | Glu | Thr | Lys | Ala | Gln | Ile | Leu | Glu | Arg | Glu | Gly | Arg | Leu | Pro |
| | 210 | | | | | 215 | | | | | 220 | | | | |
| Asp | Ala | Val | Ile | Ala | Cys | Val | Gly | Gly | Gly | Ser | Asn | Ala | Ile | Gly | Met |
| 225 | | | | | 230 | | | | | 235 | | | | | 240 |
| Phe | Ala | Asp | Phe | Ile | Asn | Glu | Thr | Asn | Val | Gly | Leu | Ile | Gly | Val | Glu |
| | | | | 245 | | | | | 250 | | | | | 255 | |
| Pro | Gly | Gly | His | Gly | Ile | Glu | Thr | Gly | Glu | His | Gly | Ala | Pro | Leu | Lys |
| | | | 260 | | | | | 265 | | | | | 270 | | |
| His | Gly | Ala | Val | Gly | Ile | Tyr | Phe | Gly | Met | Lys | Ala | Pro | Met | Met | Gln |
| | | 275 | | | | | 280 | | | | | 285 | | | |
| Thr | Glu | Asp | Gly | Gln | Ile | Glu | Glu | Ser | Tyr | Ser | Ile | Ser | Ala | Gly | Leu |
| | 290 | | | | | 295 | | | | | 300 | | | | |
| Asp | Phe | Pro | Ser | Val | Gly | Pro | Gln | His | Ala | Tyr | Leu | Asn | Ser | Thr | Gly |
| 305 | | | | | 310 | | | | | 315 | | | | | 320 |
| Arg | Ala | Asp | Tyr | Val | Ser | Ile | Thr | Asp | Asp | Glu | Ala | Leu | Glu | Ala | Phe |
| | | | | 325 | | | | | 330 | | | | | 335 | |
| Lys | Thr | Leu | Cys | Leu | His | Glu | Gly | Ile | Ile | Pro | Ala | Leu | Glu | Ser | Ser |
| | | | 340 | | | | | 345 | | | | | 350 | | |
| His | Ala | Leu | Ala | His | Ala | Leu | Lys | Met | Met | Arg | Glu | Asn | Pro | Asp | Lys |
| | | 355 | | | | | 360 | | | | | 365 | | | |
| Glu | Gln | Leu | Leu | Val | Val | Asn | Leu | Ser | Gly | Arg | Gly | Asp | Lys | Asp | Ile |
| | 370 | | | | | 375 | | | | | 380 | | | | |
| Phe | Thr | Val | His | Asp | Ile | Leu | Lys | Ala | Arg | Gly | Glu | Ile |
| 385 | | | | | 390 | | | | | 395 | | |

ENHANCED INDOLE BIOSYNTHESIS

FIELD OF THE INVENTION

The present invention relates to dye stuff biosynthesis by microorganisms, particularly the synthesis of indigo by bacteria. The present invention describes an efficient, well regulated biosynthetic system wherein a precursor for microorganismic indigo production, indole, is produced intracellularly at high levels from glucose. This indole biosynthesis is mediated by an exogenous tryptophan operon modified to promote indole production instead of tyrptophan synthesis. Indole produced in this manner can then be converted to indigo though the action of another enzymatic system followed by exposure to air. Specifically, when the modified tryptophan operon taught herein is stably transformed into a microorganism harboring an appropriate additional exogenous enzymatic pathway, indigo biosynthesis from glucose occurs when the microorganismic host strain is cultivated under appropriate conditions.

BACKGROUND OF THE INVENTION

The blue dye indigo is one of the oldest dyestuffs known to man. Its use as a textile dye dates back to at least 2,000 B.C. Until the late 1800s, indigo, or indigotin, was principally obtained from plants of the genus Indigofera, which range widely in Africa, Asia, the East Indies, and South America. As the industrial revolution swept through Europe and North America in the 1800s, demand for the dye's brilliant blue color led to its development as one of the main articles of trade between Europe and the Far East. In 1883, Alfred von Baeyer identified the chemical structure of indigo: $C_{16}H_{10}N_2O_2$. In 1887, the first commercial chemical manufacturing process for indigo was developed, and is still in use today. This process involves the fusion of sodium phenylglycinate in a mixture of caustic soda and sodamide to produce indoxyl. In the process's final step, indoxyl is then oxidized to indigo by exposure to air.

These commercial chemical processes for manufacturing indigo result not only in production of the dye itself, but also in the generation of significant quantities of toxic waste products. Obviously, a method whereby indigo may be produced without the generation of toxic byproducts is desirable. One such environmentally sound method involves indigo biosynthesis by microorganisms.

In a fortuitous discovery, Ensley et al. [(1983) *Science*, vol. 222, pp: 167–69] found that a DNA fragment from a transmissible plasmid isolated from the soil bacterium Pseudomonas putida enabled *Escherichia coli* stably transformed with a plasmid harboring the fragment to synthesize indigo in the presence of indole or tryptophan. Ensley et al. postulated that indole, added either as a media supplement or produced as a result enzymatic tryptophan catabolism, was converted to cis-indole-2,3-dihydrodiol and indoxyl by the previously identified multi-subunit enzyme napthalene dioxygenase (NDO) encoded by the *P. putida* DNA fragment. The indoxyl so produced was then oxidized to indigo upon exposure to air.

NDO had previously been found to catalyze the oxidation of the aromatic hydrocarbon napthalene to (+)-cis-(1R, 2S)-dihydroxy-1,2-dihydronapthalene [Ensley et al., (1982) *J. Bact.*, vol. 149, pp: 948–54]. U.S. Pat. No. 4,520,103, hereby incorporated by reference, describes the microbial production of indigo from indole by an aromatic dioxygenase enzyme such as NDO. The NDO enzyme is comprised of multiple subunits: a reductase polypeptide (Rd; molecular weight of approximately 37,000 daltons (37 kD)); an iron-sulfur ferredoxin polypeptide (Fd; molecular weight of approximately 13 kD); and a terminal oxygenase iron-sulfur protein (ISP). ISP itself is comprised of four subunits having an $\alpha_2\beta_2$ subunit structure (approximate subunit molecular weights: $\alpha$, 55 kD; $\beta$, 21 kD). ISP is known to bind napthalene and in the presence of NADH, Rd, Fd, and oxygen to reduce it to cis-napthalene-dihydrodiol. Fd is the rate-limiting polypeptide in this napthalene oxidation catalysis. See commonly assigned, allowed but not yet issued U.S. patent application Ser. No. 07/389,738, filed 08/04/89, hereby incorporated by reference, for a thorough discussion of the various NDO subunits and ways to improve them for purposes of indigo biosynthesis.

In addition, aromatic dioxygenases other than NDO may also be useful in the biosynthetic production of indigo. Ensley et al. also observed that a dioxygenase enzyme from another Pseudomonas strain capable of degrading toluene was also able to produce indigo when the culture media was supplemented with indole. For details, see U.S. Pat. No. 4,520,103, supra.

It has also long been known that microorganisms contain biosynthetic pathways for the production of all 20 essential amino acids, including the aromatic amino acid L-tryptophan. The de novo synthesis of aromatic amino acids (phenylalanine, tryptophan, and tyrosine) share a common pathway up through the formation of chorismate. After chorismate synthesis, specific pathways for each of the various aromatic amino acids are employed to complete their synthesis.

Bacterial biosynthesis of tryptophan from chorismate is under the control of the tryptophan (trp) operon. The trp operon, comprised of regulatory regions and five structural genes, has been extensively studied because of its complex and coordinated regulatory systems. The regulatory ant. structural organization of the trp operon, along witch the catalytic activities encoded by the structural genes of the operon, appear in FIG. 1. Of particular relevance to the present invention is the conversion of indole-3'-glycerol-phosphate (InGP), in conjunction with L-serine, to L-tryptophan. The reaction is catalyzed by the multi-subunit enzyme tryptophan synthase (TS). During the reaction, indole is produced as an intermediate. However, the indole is very rapidly combined with L-serine in a stoichiometric fashion to produce L-tryptophan. Thus, no free indole is produced as a result of this InGP plus L-serine conversion to tryptophan.

However, Yanofsky et al., (1959) *Proc. Nat'l Acad. Sci.*, vol. 45, pp: 1016–1026, identified a tryptophan synthase mutant which lead to the accumulation of indole. This particular mutant, however, was subject to spontaneous reversion to the wild-type phenotype, as the mutation resulted from a single nucleotide base pair change in a gene coding for one of subunits of tryptophan synthase.

Thus, the goal of the present invention was to create stable tryptophan synthase mutants capable of yielding high levels of intracellular indole. When such indole accumulating mutants also express an aromatic dioxygenase enzyme like NDO, this accumulated indole may be converted to indoxyl. Indoxyl so produced may then oxidize to indigo upon exposure to air. Through the commercial application of recombinant DNA technology, a novel and environmentally sound biosynthetic indigo production method has been developed utilizing microorganisms stably transformed with exogenous DNA molecules encoding a modified trp operon and an aromatic dioxygenase enzyme.

Definition of Terms

The following terms will be understood as defined herein unless otherwise stated. Such definitions include without recitation those meanings associated with these terms known to those skilled in the art.

A trp operon useful in securing microorganismic indole accumulation is a trp operon, isolated from a microorganism as a purified DNA molecule that encodes an enzymatic pathway capable of directing the biosynthesis of L-tryptophan from chorismate. Indole accumulation is enabled by modification of one or more of the pathway's structural elements and/or regulatory regions. This modified trp operon may then be introduced into a suitable host microorganism. It should be noted that the term "indole accumulation" does not necessarily indicate that indole actually accumulates intracellularly. Instead, this term can indicate that indole is produced and made available as a substrate for intracellular catalytic reactions other than the formation of L-tryptophan. In the context of this invention, the "accumulated" indole may be consumed in the conversion of indole to indoxyl by an aromatic dioxygenase such as NDO, or it may actually build up intracellularly, as would be the case when the desired end product is indole.

As used herein, "enhanced" indole accumulation refers to the intracellular production and/or accumulation of indole beyond that observed in the mutant identified by Yanofsky et al., supra, namely when asparagine is substituted for lysine at amino acid position 382 of the tryptophan synthase beta subunit polypeptide, or by a recombinant microorganism coding for that same mutation. The determination of whether enhanced indole accumulation occurred involves a comparison of indole accumulation due to new analogs in contrast to the indole accumulated under the same conditions by the analog having asparagine at amino acid position 382 of the tryptophan synthase beta subunit.

A suitable host microorganism is an autonomous single-celled organism useful for microbial indole and/or indigo production and includes both eucaryotic and procaryotic microorganisms. Useful eucaryotes include organisms like yeast and fungi. Prokaryotes useful in the present invention include bacteria such as *E. coli, P. putida*, and *Salmonella tryhimurium*.

Biosynthetic conversion of indole to indigo is meant to include indoxyl oxidation to indigo mediated by air.

A DNA molecule used herein may encode regulatory and/or structural genetic information. A DNA molecule according to the instant invention shall also include: nucleic acid molecules encoding sequences complementary to those provided; nucleic acid molecules (DNA or RNA) which hybridize under stringent conditions to those molecules that are provided; or those nucleic acid molecules that, but for the degeneracy of the genetic code, would hybridize to the molecules provided or their complementary strands. "Stringent" hybridization conditions are those that minimize formation of double stranded nucleic acid hybrids from non-complementary or mismatched single stranded nucleic acids. In addition, hybridization stringency may be effected by the various components of the hybridization reaction, including salt concentration, the presence or absence of formamide, the nucleotide composition of the nucleic acid molecules, etc. The nucleic acid molecules useful in the present invention may be either naturally derived or synthetic.

An "exogenous" DNA molecule is one that has been introduced into the host microorganism by a process such as transformation, transfection, conjugation, electroporation, etc. Please note that it is possible that the host cell into which the "exogenous" DNA molecule has been inserted may itself also naturally harbor molecules encoding the same or similar sequences. For example, when *E. coli* is used in this invention as the host strain, it is recognized that normally the host naturally contains, on its chromosome, a trp operon capable of directing the synthesis of L-tryptophan from chorismate under conditions enabling trp operon expression. A molecule such as this is referred to as an "endogenous" DNA molecule.

A stably transformed microorganism is one that has had one or more exogenous DNA molecules introduced such that the introduced molecules are properly maintained, replicated, and segregated. Stable transformation may occur by chromosomal integration or by extrachromosomal element, such as a plasmid vector. A plasmid vector is capable of directing the expression of polypeptides encoded by particular DNA molecules. Expression is regulated by an inducible (or repressible) promoter that enables high levels of transcription of functionally associated DNA molecules encoding specific polypeptides, such as the structural genes of a trp operon modified as described herein.

The following three-letter abbreviations for the 20 essential amino acid residues are used throughout the specification: Ala (Alanine), Arg (Arginine), Asn (Asparagine), Asp (Aspartic acid) , Cys (Cysteine), Glu (Glutamic acid), Gln (Glutamine), (Glycine) , His (Histidine), Ile (Isoleucine) , Leu (Leucine) , Lys (Lysine) , Met (Methionine) , Phe (Phenylalanine) , Pro (Proline), Ser (Serine) , Thr (Threonine), Trp (Tryptophan), Tyr (Tyrosine), and Val (Valine) .

SUMMARY OF THE INVENTION

One aspect of the present invention is to provide DNA molecules encoding polypeptide analogs of a tryptophan synthase beta subunit. When such analogs are incorporated into tryptophan synthase, indole accumulates intracellularly at levels in excess of that observed when lysine is replaced by asparagine at amino acid position 382 of the beta subunit. Typically, the tryptophan synthase beta subunit analogs are encoded by DNA molecules wherein at least one codon corresponding to a specific amino acid position in the DNA molecule's expression product has been substituted for another codon. Particularly useful codon substitutions can be made at the codons corresponding to amino acid positions $trpB^{379}$ and $trpB^{382}$. At the codon corresponding to the amino acid position $trpB^{379}$, those codons that can be substituted include those coding for Val, Ile, Leu, Ala, and particularly Pro. In contrast, useful codon substitutions at the codon corresponding to the amino acid position $trpB^{382}$ include those coding for Gly and particularly for Met. DNA molecules comprising codon substitutions at both codons corresponding to amino acid positions $trpB^{379}$ and $trpB^{382}$ also result in the production of enhanced amounts of intracellular indole, particularly when the codon corresponding to amino acid position trpB[379] codes for Pro and the codon corresponding to amino acid position trpB[382] codes for Met.

Another aspect of the invention provides for a tryptophan synthase beta subunit analog which, when assembled into tryptophan synthase, results in enhanced indole accumulation relative to a tryptophan synthase comprising a tryptophan synthase beta subunit Asn[382] analog. In one embodiment, the tryptophan synthase beta subunit analog comprises a substitution of one amino acid residue for another at one or more amino acid positions in the natural tryptophan synthase beta subunit amino acid sequence. Particularly useful amino acid residue substitutions include those at amino acid positions 379 and 382 of the natural tryptophan synthase beta subunit amino acid sequence. Amino acid residue substitutions at amino acid position 379 include Val, Ile, Leu, Ala, and particularly Pro in place of Arg, while at amino acid position 382, Gly and particularly Met can be substituted for Lys. In a preferred embodiment of the tryptophan synthase beta subunit analog, Pro is substituted for Arg at amino acid position 379 and Met is substituted for Lys at amino acid position 382.

A further aspect of the invention is the stable transformation or transfection of a procaryotic or eucaryotic host cell with the DNA molecules taught herein in a manner allowing the host cell to express the encoded tryptophan synthase beta subunit under appropriate conditions. The procaryotic host *Escherichia coli* represents one such preferred host microorganism.

A biologically functional plasmid or viral DNA vector including a DNA molecule of the invention represents another aspect of this invention. In one embodiment, a eucaryotic or procaryotic host cell, such as *E. coli*, is stably transformed or transfected with such a biologically functional vector.

Other aspects of the invention involve methods for the biosynthesis of indole and indigo using the DNA molecules of the invention. Microorganismic indole production can be accomplished by stably transforming or transfecting a host microorganism with a DNA molecule of the invention and cultivating the microorganism under conditions enabling the biosynthesis of indole. Similarly, indigo can be produced by further transformation or transfection of the above microorganism with a DNA molecule encoding an aromatic dioxygenase enzyme, such as napthalene dioxygenase. Cultivating the microorganism under conditions facilitating the expression of the DNA molecules encoding the tryptophan synthase beta subunit analog and the aromatic dioxygenase enables intracellular indole accumulation and conversion of indole to indoxyl, which is then oxidized to indigo by exposure to air.

Numerous aspects and advantages of the invention will be apparent to those skilled in the art upon consideration of the following detailed description which provides illumination of the practice of the invention in its preferred embodiments.

DETAILED DESCRIPTION

Present methods of biosynthetic indigo production employ only the bioconversion of indole to indigo utilizing an aromatic dioxygenase like NDO. This necessitates the addition of indole to the culture media, as no intracellular indole accumulation occurs in such systems. However, indole added to the culture media may be toxic to microorganisms. *E. coli* growth may be inhibited when indole is present in the media. Bang et al. [(1983) *Biotechnology and Bioengineering*, vol. 25, pp: 999–1011] described the effects of adding exogenous indole to *E. coli* being grown in shake flasks in minimal media. They found that while concentrations of up to 0,025% slowed bacterial growth, the cells acclimated to the presence of indole over time. However, 0.03% indole severely limited growth with no apparent acclamation, and indole concentrations above 0.04% prohibited growth altogether. In addition, Bang et al., supra, found that L-tryptophan synthesis was inhibited when indole was added at concentrations in excess of 0.2 g/100 ml.

To avoid the inherent limitations of indigo synthesis through indole media supplementation, a system capable of endogenous indole biosynthesis is required. One such system may employ transferring an exogenous DNA molecule encoding a DNA sequence for a trp operon, modified so as to promote indole production and accumulation, into a recombinant host microorganism already capable of expressing NDO (preferably altered as discussed above). Such a system would allow for the production of indigo from glucose or other carbon sources. Optimally, such a system would efficiently convert the endogenously produced indole to indoxyl in a manner avoiding intracellular indole accumulation.

Figure 1:
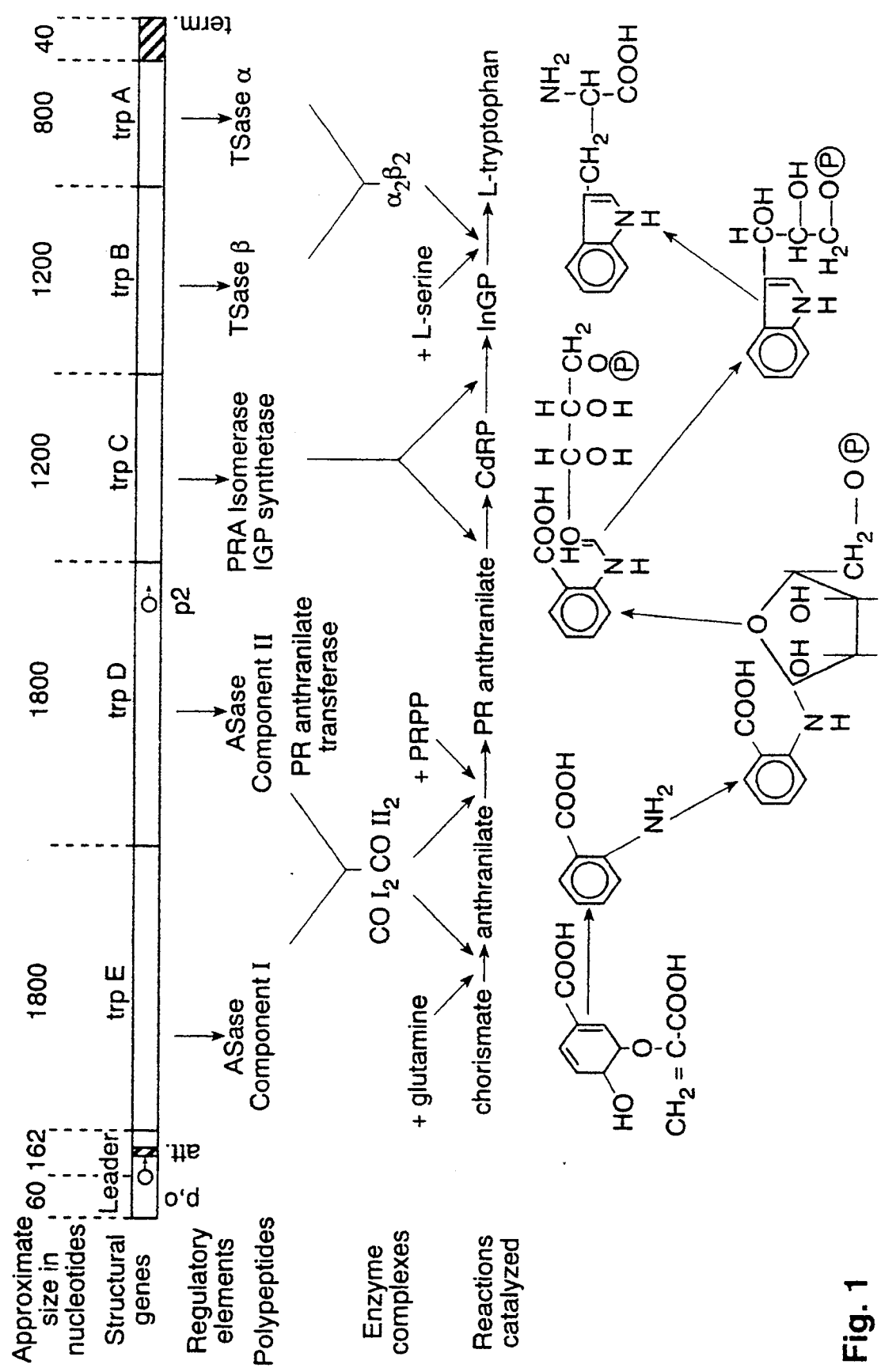
FIG. 1 provides a physical map identifying the various regulatory and structural elements of the *E. coli* trp operon. Additionally, the various proteins encoded by the structural genes and the chemical reactions catalyzed thereby are also described.

It has long been known that indole is produced as an intermediate in L-tryptophan biosynthesis. However, the indole so produced exists only transiently, i.e. it exists only during the bioconversion of InGP and L-serine to L-tryptophan. No soluble free indole accumulates as a result of this bioconversion, which is catalyzed by the multi-subunit enzyme tryptophan synthase (TS). TS is one of several enzymes encoded by the trp operon and has been extensively studied. For example, see Hyde et al., (1990) *Biotechnology*, vol. 8, pp: 27–32; Djavadi-Ohaniance et al., (1986) *Biochemistry*, vol. 25, pp: 2502-08; and Ahmed et al., (1986) *Biochemistry*, vol. 25, pp: 3118-24. The reactions catalyzed by the five gene products encoded by the trp operon are depicted in FIG. 1.

TS is comprised of an $\alpha_2\beta_2$ subunit structure. The $\alpha$ subunit catalyzes the conversion of InGP to indole and D-glyceraldehyde 3'-phosphate and has an approximate molecular weight of 29 kD. The $\beta$ subunit, which has an approximate molecular weight of 43 kD and catalyzes the reaction L-serine plus indole to make L-tryptophan, liberating one molecule of $H_2O$ in the process. The $\beta$ subunits exist as a dimer, called the $\beta_2$ subunit. $\beta_2$ associates with two $\alpha$ subunits to form the $\alpha_2\beta_2$ TS holoenzyme which has an extended $\alpha\beta\beta\alpha$ quaternary structure. The holoenzyme catalyses the reaction of L-serine plus InGP to produce L-tryptophan, D-glyceraldehyde 3'-phosphate, and one molecule of $H_2O$. No free indole is produced because it is a "channeled" intermediate, i.e.

indole produced at the α subunit active site is intramolecularly transferred by internal diffusion to the β subunit active site [Hyde et al., (1990) supra]. TS mutants unable to properly channel indole from the α subunit active site to the β subunit active site, or that have an altered β subunit active site, may be unable to combine L-serine with indole and thus may be useful in indigo biosynthesis as free soluble indole may be provided upon which NDO can act.

The DNA sequence of the *E. coli* trp operon was published in 1981 by Yanofsky et al. [*Nucl. Acids Res.*, vol. 9, no. 24, pp:6647–6668]. The five structural genes of operon are transcribed as one polycistronic message of about 6,800 ribonucleotides in length. The 5'-most gene, trpE, is encoded by nucleotides 279–1841 of this polycistronic messenger RNA (mRNA). Nucleotides 1841–3436 code for the trpD gene product, while trpC is coded for by nucleotides 3440 to 4798. Because TS is the enzyme known to produce and then utilize indole in the production of tryptophan, the genes encoding the α and β subunits, namely the trpA (mRNA nucleotides 6003–6809) and trpB (mRNA nucleotides 4810–6003) genes, respectively, may be subcloned into an appropriate vector so that site directed mutagenesis may be conducted so as to render the resultant TS holoenzyme incapable of combining indole with serine to produce tryptophan.

As previously noted, a point mutation near the carboxy terminus (C-terminus) of the trpB gene, [SEQ ID Nos. 4 and 5], specifically at amino acid position 382, was observed by Yanofsky et al., supra, (1959) to lead to intracellular indole accumulation. Later, this single nucleotide change was found to have occurred at the third nucleotide position in the codon normally coding for lysine. This mutation resulted in asparagine being substituted for lysine at this position. Because of this mutation's third position character and deleterious effect on the cell's ability to synthesize tryptophan, it was very unstable and subject to reversion to the wild type genotype. Accordingly, to avoid spontaneous reversion to the wild type sequence, any engineered mutation will preferably involve more than one nucleotide base pair change whenever possible.

The widely known technique of site directed mutagenesis provides a ready mechanism whereby the lysine to asparagine change at the codon corresponding to amino acid position 382, designated as $Lys^{382}$ to $Asn^{382}$, of the trpB gene can be stabilized. One such stabilized form involves the generation of a double mutant at this particular codon, corresponding to trpB amino acid position 382 ($trpB^{382}$), thus effectively preventing spontaneous reversion to the wild type genotype and phenotype. Additionally, as a substitution at this particular trpB residue was observed to lead to intracellular indole accumulation, other amino acids may also be substituted at this position in an effort to improve or enhance indole accumulation. For example, substitutions may be made based on differences in side chain charge or size. One such preferred change involves the substitution of glycine for lysine at $trpB^{382}$. In another preferred embodiment, methionine may be substituted for lysine at this position, although this particular substitution, while leading to greater indole accumulation than the $Asn^{382}$ substitution of Yanofsky et al., supra, (1958) produces less indole than the $Gly^{382}$ mutation.

Amino acid substitutions at positions other than $trpB^{382}$ may also prove useful in generating indole-accumulating mutants. For instance, amino acid substitution at $trpB^{379}$, represented by arginine in the wild type β subunit, may lead to an even more significant level of indole accumulation. Useful amino acid substitutions at $trpB^{379}$ may include replacing the wild type residue with Ala, Ile, Leu, Pro, or Val, in addition to other amino acid residues. In fact, when proline is substituted for arginine at $trpB^{379}$, indole is seen to accumulate intracellularly to a level 20 times that found for the Yanofsky et al. mutation. It is likely that other amino acid positions in trpB can also be mutagenized favorably with respect to indole accumulation. Other potential useful changes may include disrupting the indole "channel," thus preventing the movement of indole from the α subunit to the β subunit of the tryptophan synthase holoenzyme. Likewise, one or more amino acid substitutions at residues believed to be involved in the conversion of indole and L-serine to L-tryptophan in the β subunit are also possible. See Hyde et al., supra, (1990).

It should be noted that in addition to amino acid substitutions at particular amino acid residues, the present invention also envisions the insertion of additional amino acid residues at one or more particular positions as well as the deletion of one or more specific residues. In addition, combinations of various useful mutations causing increased indole accumulation, such as amino acid substitutions, insertions, and/or deletions, also fall within the scope of this invention. One such double mutant, designated pYTrp#26, incorporates amino acid substitutions at two different positions. Specifically, pYTrp#26 represents the following changes from the wild type β subunit: $Arg^{379}$ was changed to $Pro^{379}$ and methionine was substituted for lysine at $trpB^{382}$.

Beyond the above trpB mutations, other mutations within the trp operon may also prove useful in enabling microorganismic indole accumulation. Of particular interest are mutations in the trpA gene, which upon expression may still result in a subunit capable of assembly into the TS holoenzyme and catalyzing the conversion of InGP to indole and D-glyceraldehyde-3'-phosphate, but being incapable of participating in the requisite indole "channeling" required for L-tryptophan synthesis. Also, because the β subunits of the TS holoenzyme comprise approximately two-thirds of the indole "channel," [Hyde et al., supra, (1990)] mutations which deleteriously affect this region's ability to facilitate indole "channeling" are also envisioned by the present invention. Further, site-directed mutagenesis may be used to engineer amino acid substitutions, deletions, and/or insertions in the active site of the β subunits. For example, an amino acid substitution at $Lys^{87}$ in the β subunit may produce a β subunit still capable of assembling into the TS holoenzyme, but that is incapable of catalyzing the bioconversion of L-serine and indole to L-tryptophan.

In addition to making specific amino acid changes in the various polypeptides encoded by the genes of the trp operon, site-directed mutagenesis may be employed to alter the structural organizational and/or regulatory regions of the trp operon. The operon's regulatory systems are complex and coordinated, being comprised of at least three levels of regulation. At the protein level, in the presence of excess L-tryptophan, anthranilate synthase, a multi-subunit enzyme whose subunits are encoded by the trpE and trpD genes, experiences feedback inhibition [Henderson et al., (1970) *J. Biol. Chem.*, vol. 245, pp:1416–1423]. At the transcriptional level, in the presence of excess L-tryptophan, activated trp repressor molecules limit transcription initiation to about 1% of its maximal rate. Under these conditions, attenuation (for an explanation, see Yanofsky, C. (1987) *TIG*, vol. 3, no. 12, pp: 356–360; Yanofsky et al., (1981) supra), involving both transcriptional and translational regulation, can suppress structural gene transcription another six-fold, although a significant basal level of trp operon expression still occurs when excess L-tryptophan is present [Roesser et al., (1989) *J. Biol. Chem.*, vol. 264, no. 21, pp: 2284–2288]. Thus, mechanisms enabling more stringent transcriptional and/or translational control may be useful with respect to indole and indigo biosynthesis.

Removal of the endogenous trp promoter from plasmid constructions harboring the trp operon may provide for enhanced regulatory control. In one embodiment, the 7.4 kb Eco RI - Sal I fragment encoding the trp operon may be cloned into the expression vector pAC1, the construction of which is described in detail in U.S. patent application Ser. No. 07/389,738, supra. This construction is designated pYTrp. The pAC1 plasmid vector employs the heat-inducible phage lambda $P_L$ promoter to direct the expression of DNA sequences inserted proximately downstream. Please note that expression systems employing the $P_L$ promoter require the presence of the repressor protein mutant $cI_{857}$ for appropriate regulation. The low-level, constitutively expressed gene encoding $cI_{857}$ may be inserted into the chromosome of an appropriate host strain, such as *E. coli* strain FM5 (A.T.C.C. accession no. 53911) or it may be plasmid borne.

Constructions such as pYTrp may be modified to include the various mutants alluded to in this invention. In one embodiment, designated pYTrp#26, a DNA fragment encoding a modified trpB gene encoding a polypeptide capable of producing elevated levels of intracellular indole was subcloned into pYTrp after excision of the wild type sequence. When cultivated in a 1 L (liter) fermentor, pYTrp#26 produced about 30% of its total yield of indole prior to $P_L$ temperature induction. When the endogenous trp promoter was removed from the pYTrp#26 construct by removing about 400 bp (base pairs) of upstream, non-coding trp operon DNA, the new construction, pYTrp#26p-, showed considerably tighter regulation and enhanced host cell growth as compared to a bacterial strain harboring pYTrp#26.

However, the pYTrp#26p- construct still contained the trp attenuator region, which may be responsible for up to 90% of trp operon repression in vivo. In a preferred embodiment, a plasmid, designated pYTrp#26att-, was constructed in which both the trp promoter and attenuator regions are deleted from the exogenous trp operon construct. Thus, the structural genes for the indole-producing trp operon construction can be regulated solely by the promoter designed to drive the expression of inserted heterologous DNA sequences when such sequences are cloned into the expression vector. To further optimize expression of the inserted trp structural genes, a strong ribosomal binding site with consensus spacing can be inserted between the expression vector's promoter, such as the $P_L$, and the 5' end of the trpE gene.

Plasmids other than pAC1 may also be useful in practicing the present invention. The entire trp operon, or one of the preferred variants taught herein, may be inserted into a plasmid such as pBR322. In one embodiment, a construction designated pBRYTrp (containing the entire trp operon from pYTrp#26p-) was generated. Such constructions may exhibit enhanced, or in the case of pBRYTrp#26p-, reduced expression control of the inserted DNA sequence(s). Reduced control of expression (prior to thermal induction) in cases where high copy number plasmids such as pBR322 are used in conjunction with the $P_L$ promoter is perhaps due to titrating out the small number of $cI_{857}$ repressor molecules present in the host cell. Accordingly, when moderate to high copy number plasmids are used in accordance with this invention, externally regulated promoters other than $P_L$ may prove useful.

Another modification one may make to an indole-producing trp operon is to delete, in whole or in part, the 3' untranslated portion of the operon. In *E. coli*, as well as in the 7.4 kb fragment used as the starting material in this invention, this 3' region contains both a rho-dependent and rho-independent transcription termination sequence. Removal of either or both of these sequences may be readily accomplished by those skilled in the art. In one embodiment of the present invention, only the rho-dependent terminator is eliminated, deleting approximately 250 bp 3' of the trpA gene. However, should both termination sequences be removed, it is preferable that another termination sequence present in the vector DNA be functionally associated with the 3' end of the inserted trp operon to insure efficient transcription termination.

Other useful modifications of a trp operon useful in the practice of the present invention may also be made. For example, in the naturally *E coli* trp operon, it has been observed that the initiator codon of the trpD and trpA genes overlap with the termination codons of the trpE and trpB genes, respectively. The DNA sequence, 5'-TGATG-3', involved in these overlaps is identical. Yanofsky et al., supra, (1981). This overlap has been referred to as "translational coupling" and is perhaps an evolutionarily evolved device used in the translation of polycistronic mRNAs to ensure proportionate production of functionally related polypeptides or equimolar production of proteins that are constituents of a multi-enzyme complex. Das et al., (1984) *Nucl. Acid Res.*, vol. 12, no. 11, pp: 4757–4768. The translation products of both the trpE/trpD and trpB/trpA messages form $\alpha\beta\beta\alpha$ complexes. In contrast, the trpC gene, the only member of this operon which does not code for a polypeptide incorporated into a multi-subunit enzyme, does not overlap with either the trpD gene terminator or the trpB initiation sequences. Instead, the trpC gene is flanked by six untranslated nucleotides at its 5' end and 14 untranslated nucleotides at its 3' end.

It may be desirable to eliminate the overlaps present in the trpE/trpD and trpB/trpA sequences. This may be accomplished by manufacturing a small synthetic double stranded DNA fragment spanning two restriction sites or by site directed mutagenesis. Using either approach, the inserted DNA sequence may be designed to physically separate the termination and initiation codons of the various genes. The sequence intervening between the termination and initiation codons may merely serve as a spacing sequence. However, Das et al., supra, suggest mere separation of translationally coupled messages can lead to decreased levels of the translation products. Thus, any separation performed on these overlapping sequences should not be for mere spacing. Instead, such sequences should be designed so that upon termination of translation of the more 5' message, translation initiation of the more distal gene by the same ribosome is possible. Thus, a ribosomal binding site, and/or one or more restriction enzyme recognition sequences to improve the clonability of the various trp operon genes, might be included in such a spacer region. Additionally, the untranslated regions flanking the trpC gene could also be modified to include one or more of the above mentioned possibilities.

It is known that the trp operon contains at least six ribosomal binding sites, also known as Shine-Delgarno sequences [Yanofsky et al., supra, (1981)]. Each of the five trp structural genes and the leader sequence (comprising the attenuator) are each preceded by such a sequence. However, in the case of trpD, trpC, trpB, and trpA, the Shine-Delgarno sequence is located within the coding region of the gene immediately preceding it. Thus, in an effort to optimize translation efficiency, as suggested in the previous paragraph, it may be preferable to modify the operon such that each gene be sufficiently removed from the others so as to allow for ribosomal binding sites in untranslated regions immediately adjacent to the 5' end of each gene. Such modifications could be conducted for any one, some, or all of the five trp structural genes, although in the cases of the trpE/trpD and trpB/trpA genes, attention would have to be directed at maintaining termination and initiation codons.

The trp operon is de-repressed in $E.$ $coli$ only when the organism encounters an environment depleted or devoid of tryptophan, although a continuous low level of expression is observed at all times in order to respond to environmental stress. As a result of this only intermittent de-repression, the codon usage observed in the coding regions of the trp structural genes is characteristic of that seen in other moderately expressed $E.$ $coli$ genes, namely it is non-random but less restricted than the codon usage observed in highly expressed $E.$ $coli$ genes. Because the goal of this invention is the development of an efficient, commercially viable biosynthetic indigo production system, it may be preferred to enable a rate of indole synthesis in excess of that which is possible using a modified, albeit mostly natural, trp operon. Along these lines, one may construct a trp operon that incorporates, in whole or in part, only codons found in highly expressed $E.$ $coli$ proteins. These codons, often called "preferred" codons, are widely known in the art. To generate such an optimized operon, or a part thereof, one could employ the procedures described by Stabinsky, U.S. Pat. No. 4,897,471, hereby incorporated by reference. Should a host other than $E.$ $coli$ be used, such as a yeast or other bacterial strain, it would be desirable to utilize codons preferred by that organism in constructing a trp operon in accordance with this invention.

All major microbial groups possess the ability to synthesize tryptophan under appropriate conditions. All enteric bacterial species appear to harbor trp operons structurally organized as that found in $E.$ $coli$. Other types of bacteria have the genes encoding the various trp operon components at various chromosomal locations. The elements of such dispersed systems may be independently regulated as well. In addition, the various components of the trp operons in such microorganisms potentially contain genes coding for polypeptides having varying degrees of amino acid homology when compared to their counterparts in $E.$ $coli$. For example, the trpA gene found in the close $E.$ $coli$ relative $S.$ $typhimurium$ is 85% homologous at the nucleotide level and 96% homologous at the amino acid level when compared to the trpA gene and protein from $E.$ $coli$. It is likely that greater differences exist with other microorganisms that are more distantly related to $E.$ $coli$. Thus, within the scope of this invention the possibility exists that a highly efficient hybrid trp operon could be constructed incorporating components from various microorganismic trp operons and that when such a hybrid operon is modified as is taught herein, it could be more efficient in the high level production of indole than any modified but unhybridized trp operon.

Because microorganismic indigo biosynthesis, absent indole-supplemented media, requires that the microorganism be able to synthesize exogenous enzymatic pathways capable both of producing indole and then catalyzing indole's conversion to indoxyl, various combinations of plasmids encoding these different pathways may be utilized. To insure proper maintenance, segregation, and propagation of an indigo producing system employing more than one plasmid, the plasmids used must be from different complementation groups. In addition, transcription of the genes of the two pathways may be under the control of a single type of promoter, such that upon induction, both pathways are transcribed. For example, in a two plasmid system, expression of both pathways may be under the control of the $P_L$ promoter or a suitable alternative. Alternatively, each pathway may be under the control of a promoter induced by a different mechanism. Such a system would enable the induction of the two pathways at different times, if desired. In this way, indole accumulation could begin prior to NDO synthesis. Alternatively, NDO could be synthesized prior to transcription and translation of the modified trp operon, perhaps to enable the conversion of indole to indigo without allowing intracellular indole to accumulate to toxic levels prior to its bioconversion to indoxyl.

Also within the scope of the invention is the generation of a single plasmid system upon which both enzymatic pathways are harbored. Again, in such a system, each pathway may employ a promoter of the same type, thus enabling simultaneous expression of both operons. However, it is also possible that each pathway could employ a promoter inducible by independent mechanisms, thus enabling the induction of each pathway simultaneously or at different times. In yet another aspect, both pathways may be functionally associated so that only one promoter need be employed. This single promoter would enable transcription of both operons. The operons could be arranged so that the NDO pathway is adjacent to the regulatable promoter, followed by the trp operon. Likewise, the trp operon could be inserted before the NDO operon.

Additionally, it is possible to develop microorganismic indole and/or indigo producing systems wherein one or more of the genes encoding polypeptides involved in these processes are integrated into the chromosome of the host microorganism, as opposed to being located on one or more extrachromosomal elements. Rapid and irreversible chromosomal integration can be directed by an integration plasmid designed to deliver into the host microorganism's chromosome (via recombination) cloned DNA molecules. Such integration plasmids, containing the DNA molecules intended to be integrated, are transformed into the desired host microorganism. Such plasmids are capable of maintenance, propagation, segregation, and copy number control. In addition, selectable markers, such as one or more drug resistance genes, may be included. Essential is the inclusion of integration sequences capable of directing the translocation event. Such integration sequences may be obtained from a variety of bacteriophage and plasmid sources. The DNA molecules intended to be translocated will comprise, in addition to the desired structural gene(s), the requisite regulatory genes and/or elements required for proper expression regulation of the included structural genes. Once integrated, the trp operon gene(s) and/or aromatic dioxygenase encoding molecule(s) may be expressed under appropriate conditions, thereby facilitating intracellular indole production and/or indigo biosynthesis.

The general recombinant DNA techniques used in the present invention, like DNA isolation and purification, cleavage of DNA with restriction enzymes, construction of recombinant plasmids, introduction of DNA into microorganisms, and site directed mutagenesis, are described in many publications, including Manniatis et al., *Molecular Cloning - A Laboratory Manual*, Cold Spring Harbor Laboratory (1982) and *Current Protocols in Molecular Biology*, edited by Ausubel et al., Greene Publishing Associates and Wiley Interscience (1987).

The following examples are offered to more fully illustrate the present invention. In addition, the Examples provide preferred embodiments of the present invention but are not meant to limit the scope thereof.

Cloning of the Hpa I/Bam HI fragment generated the intermediate plasmid p1036A/B. p1036A/B was then digested with Eco RI and Bam HI and the 1,200 bp fragment carrying the desired sequence was gel purified. The resultant gel-purified fragment was then ligated into similarly digested M13mp11 RF DNA and transformed into competent *E. coli* JM109 by standard techniques. A plaque found to contain the desired construct was isolated and designated mpA/B. Single stranded (SS) DNA was then prepared from mpA/B to serve as the substrate for site-directed mutagenesis according to standard procedures.

As it was known that a particular trpB point mutation at the codon corresponding to amino acid position 382 (whereby Asn was substituted for Lys) had previously been observed to result in the production of detectable levels of intracellular indole [Yanofsky et al., supra, (1959),], oligonucleotides were designed and synthesized to enable the substitution of the wild type residue for another at this position. As the DNA sequence of the trp operon, and the trpB gene in particular, has been described in the literature, the design of oligonucleotides useful herein is readily within the skill of the art. The trpB DNA sequence [SEQ ID NO:3], and the corresponding amino acid sequence, that is of particular relevance to the present invention is as follows:

```
         Val Asn Leu Ser Gly Arg Gly Asp Lys Asp Ile Phe
5' -     GTT AAC CTT TCC GGT CGC GGC GAT AAA GAC ATC TTC
                             379         382
```

EXAMPLE 1

Trp Operon Cloning

The 7.4 kb fragment encoding the entire trp operon was excised from plasmid pGX50 (NRRL B-12264) using Eco RI to Sal I. Following agarose gel purification, this fragment was then ligated into pAC1 which had previously been digested with Eco RI and Xho I and then phosphatased to prevent reannealing of vector and polylinker. The resultant plasmid construct was designated pYTrp.

EXAMPLE 2

Generation of trpB Indole-accumulating Mutants

To generate a trp operon capable of directing the high level accumulation of intracellular indole, pYTrp was then digested with Hpa I and Bam HI, releasing a 1.2 kb fragment containing the C-terminal region of the trpB gene in conjunction with the entire trpA gene. Following agarose gel purification of the Hpa I/Bam HI fragment, it was ligated into plasmid p1036 which had been previously digested with Hpa I and Bam HI. p1036 was generated by substituting the Sst I to Aat II fragment (containing a Kanamycin resistance gene) of pCFM836 (see U.S. Pat. No. 4,710,473, hereby incorporated by reference) with a similar fragment from pCFM636 (U.S. Pat. No. 4,710,473, supra) and by substituting the DNA sequence between the unique Aat II and Eco RI (containing a synthetic $P_L$ promoter) restriction sites with the following oligonucleotide duplex:

SEQ ID NO: 1: 5'    CATCGATTCTAG    3'
SEQ ID NO: 2: 3' TGCAGTAGCTAAGATCTTAA 5'

Each engineered substitution was designed to alter at least two contiguous nucleotides, thus substantially reducing the likelihood of a reversion to the wild type genotype. With these oligonucleotides in hand, site-directed mutagenesis was then conducted using SS mpA/B DNA.

Following the mutagenesis reactions, the products were serially diluted and transformed into competent JM109 and plated. Following an overnight incubation, plates containing several hundred plaques for each of the various mutations were overlaid with nitrocellulose, allowing phage particles to be transferred. Following denaturation and neutralization, the filters, to which the SS phage DNA was now bound, were baked under house vacuum for 2 hours at 80° C. The filters were then hybridized to radiolabelled probes as described in Manniatis et al., supra, the probe being that oligonucleotide which had been used for that specific mutagenesis reaction. Following hybridization, the filters were washed under stringent conditions [2X SSC (1X SSC=0.15M NaCl, 0.015M sodium citrate, pH 7.0), 1% sodium dodecyl sulfate (SDS), 4° C. below the theoretical melting temperature] to remove non-specific hybridization and then autoradiographed. The washing conditions used varied due to the use of probes different of different lengths and of different sequences. For the purposes of these hybridizations and washings, oligonucleotide melting temperatures ($T_M$) were calculated by allocating 2° C. for each A or T in the probe and 4° C. for each C or G, and then summing the result for each oligonucleotide.

Using the autoradiography results, putative positive plaques were isolated and subjected to at least one round of plaque purification. One or more of those plaques found to strongly hybridize to its specific probe was removed from its corresponding plate, serially diluted, and used to transfect a fresh JM109 culture in logarithmic phase. Following a brief infection period, the mixtures were then plated and allowed to grow out. The nitrocellulose binding and hybridization procedure was then conducted again for each putative mutant.

Upon confirmation by hybridization that the desired mutant had been obtained, RF DNA for each mutant was prepared. This RF DNA was then digested with Hpa I and Bam HI, thus excising a particular trpB mutant as a Hpa I to Bam HI fragment. For each mutant, this fragment could then be ligated into pYTrp which had previously been digested with Hpa I and Bam HI and gel purified. These ligation reactions were then used to transform competent E. coli strain FM5. A colony of each of the resultant transformants was then cultivated in a shaker flask under conditions allowing for the transcription and translation of the plasmid-borne trp operon genes. Such growth was accomplished by growing the culture in a minimal medium (comprised of 6 g $Na_2HPO_4$, 3 g $KH_2PO_4$, 0.5 g NaCl, and 1 g $NH_4Cl$ per liter) at 30° C. to an $OD_{600}$ of 0.3, shifting the temperature to 42° C. for 1.5 hr., and then lowering the temperature to 30° C. for 2 hr., at which time 300 µg/mL of anthranilate was added. The cultures were then grown another 7 hours before being harvested and analyzed colorometrically for intracellular indole.

The colorimetric indole assay for each mutant was conducted by extracting 500 µl of cells (as grown above) with 500 µl of toluene. Extraction was accomplished by vortexing the cells at room temperature for 5 min. The organic phase was then removed. 100 µl of the extracted organic phase was then added to 5 ml of Assay Mixture (5.56 g p-methylaminobenzaldehyde in 1 L ethanol-acid (80 ml concentrated HCl+920 ml ethanol)), vortexed, and allowed to stand at room temperature for 15-20 min., after which time the $OD_{540}$ was measured. These results were compared to a indole standard curve prepared by measuring the $A_{540}$ generated when 0, 2, 4, 6, 8, or 10 µg of indole (taken from a freshly prepared indole stock solution, 100 µg/ml $dH_2O$) was assayed as described above.

The above procedures were used to analyze a series of mutants designed to introduce a single amino acid substitution at trpB$^{382}$. In addition, mutations were also generated at the position corresponding to trpB$^{379}$. It was found that substituting Pro for the wild type residue at this position enabled more than five-fold increase in indole accumulation as compared to the best trpB$^{382}$ mutant, namely Gly$^{382}$. Because two sites were discovered to be independently capable of enabling intracellular indole accumulation, a series of double mutants, with changes at both trpB$^{379}$ and trpB$^{382}$, were generated. The various mutants generated and the amount of indole they produced appear in Table 1.

TABLE 1

| Mutant | Position | Substitution | Indole (mg/L) |
| --- | --- | --- | --- |
| 1 | 382 | Asn | 7 |
| 2 | 382 | Ser | 0 |
| 3 | 382 | Ala | 0 |
| 4 | 382 | Thr | 0 |
| 5 | 382 | Gly | 30 |
| 6 | 382 | Gln | 0 |
| 7 | 382 | Arg | 0 |
| 8 | 382 | Glu | 0 |
| 9 | 382 | Phe | 0 |
| 10 | 382 | Met | 18 |
| 11 | 379 | Pro | 160 |
| 12 | 379 | Pro | |
|  | 382 | Met | 150 |

TABLE 1-continued

| Mutant | Position | Substitution | Indole (mg/L) |
| --- | --- | --- | --- |
| 13 | 379 | Gly | |
|  | 382 | Gly | 7 |

However, none of the double mutants generated showed any increased ability to accumulate indole relative to Pro$^{379}$, although in the Pro$^{379}$/Met$^{382}$ double mutant, designated pYTrp#26, 150 mg/L indole was detected. This indole level was roughly the same as was detected in the best single mutant, Pro$^{379}$ DNA sequencing was performed on each of the indole accumulating mutants to confirm the presence of the anticipated changes. Because pYTrp#26 produced nearly as much indole as any single mutant, it was chosen for further study, as a reversion to the wild type phenotype and/or genotype was much less likely to occur in a double mutant.

EXAMPLE 3

Fermentation of Indole Accumulating

As shake flask studies indicated that substantial quantities of intracellular indole could be produced by pYTrp#26, small scale fed batch fermentations were conducted with this and other constructs to examine indole production and accumulation in a more realistic industrial setting. The fed-batch fermentations were conducted in a small, 1 L chemostat under carbon-limited growth conditions. The initial batch medium was prepared in a 2 L sterile bottle by combining previously prepared, sterile solutions. The medium was prepared by combining 200 ml of Solution I (6 g yeast extract plus $dH_2O$ to a final volume of 200 ml), 200 ml of Solution 2 (3.75 g $(NH_4)_2SO_4$, 8.4 g $K_2HPO_4$, and 4.6 g $KH_2PO_4$ plus $dH_2O$ to a final volume of 200 ml), 15 ml of a 40% glucose solution, 4.8 ml of 1M $MgSO_4$, 2.4 ml of a trace metals solution (Table 2), 2.4 ml of a vitamins and minerals solution (Table 3), 775 ml $dH_2O$, ampicillin to 100 µg/ml, and 200 µl of antifoam.

TABLE 2

| Trace Metals Solution | |
| --- | --- |
| Compound | g/L |
| $FeCl_3.6H_2O$ | 27.0 ± 0.3 |
| $ZnCl_2$ | 2.0 ± 0.03 |
| $CoCl_2.6H_2O$ | 2.0 ± 0.03 |
| $NaMoO_4.2H_2O$ | 2.0 ± 0.03 |
| $CaCl_2.2H_2O$ | 1.0 ± 0.02 |
| $CuSO_4.5H_2O$ | 1.9 ± 0.03 |
| $H_3BO_3$ | 0.5 ± 0.01 |
| $MnCl_2.4H_2O$ | 1.6 ± 0.03 |
| Sodium Citrate.$2H_2O$ | 73.5 ± 1.0 |

[prepare by dissolving the ingredients in about 90% of the total lot volume with purified $H_2O$; after dissolution, adjust to the desired final lot volume using purified $H_2O$; sterilize by filtration through a 0.2 µn filter]

TABLE 3

| Vitamins and Minerals Solution | |
| --- | --- |
| Compound | |
|  | g/L |
| Biotin | 0.06 ± 0.001 |
| Folic Acid | 0.04 ± 0.001 |
| Pyridoxine | 1.4 ± 0.03 |
| Riboflavin | 0.42 ± 0.008 |
| Pantothenic Acid | 5.4 ± 0.11 |
| Niacin | 6.1 ± 0.12 |
|  | ml/L |

TABLE 3-continued

Vitamins and Minerals Solution

| Compound | |
|---|---|
| 10N NAOH | 5.31 ± 0.11 |

[prepare by: (a) dissolving Biotin, Folic Acid, and Riboflavin in about 4% of total lot volume using purified H2O and 5.65±0.19% of total lot volume of 10 N NaOH; after dissolution, adjust to 5% of total lot volume using purified H2O; (b) dissolve Pryidoxine and Niacin in about 2% of total lot volume using purified H2O and 94.2±0.19% of total lot volume of 10 N NaOH; after dissolution, adjust to 2.5% of total lot volume using purified H2O; (c) dissolve Pantothenic Acid in about 2% of total lot volume using purified H2O and 0.188±0.019% of total lot volume of 10 N NaOH; after dissolution, adjust to 2.5% of total lot volume using purified H2O; (d) combine the solutions prepared in (a), (b), and (c) and adjust to the total lot volume using purified H2O; and (e) sterilize the solution by filtration through a 0.2 μm filter]

The batch medium was then added to a previously sterilized chemostat and preheated to 30° C. Agitation was set at 1,000 rpm, the air flow rate was set at 3 L/min, and the pH controller was set to maintain a solution pH of 7.0±0.2 by adding either $H_3PO_4$ or $NH_4OH$. The fermentor was then inoculated to a final $OD_{600}$ of about 0.02–0.03 using a fresh overnight culture. The culture was allowed to grow at 30° C. until an $OD_{600}$ of about 8.7 was reached. At that point, the addition of a feed solution[1] was initiated according to the following schedule:

[1] in a sterile 500 ml bottle, add the following previously sterilized solutions: 60 ml of Solution 3 (15 g yeast. extract, 15 g bacto-tryptone, and dH2O to 60 ml); 160 ml of a 63.5% glucose solution; 8 ml of 1M MgSO4, 2 ml of trace metals, supra; 2 ml of vitamins and minerals, supra; and ampicillin to a final concentration of 100 μm/mL.

| $OD_{600}$ | Feed rate (ml/hr) |
|---|---|
| 8.7 | 1.25 |
| 14.9 | 1.9 |
| 19.8 | 3.1 |
| 24.8 | 5.0 |
| 37.2 | 7.5 |
| 62.0 | 11.25 |
| 74.0 | 20.0 |
| 86.8 | 25.0 |

When the culture reached an $OD_{600}$ of 65 to 75, transcription of the modified trp operon was induced by shifting the culture temperature to 42° C. for 1.5 hr. After induction, the culture's temperature was quickly adjusted down to 30° C. The fermentation was then continued for another 8 hr.

Figure 2:
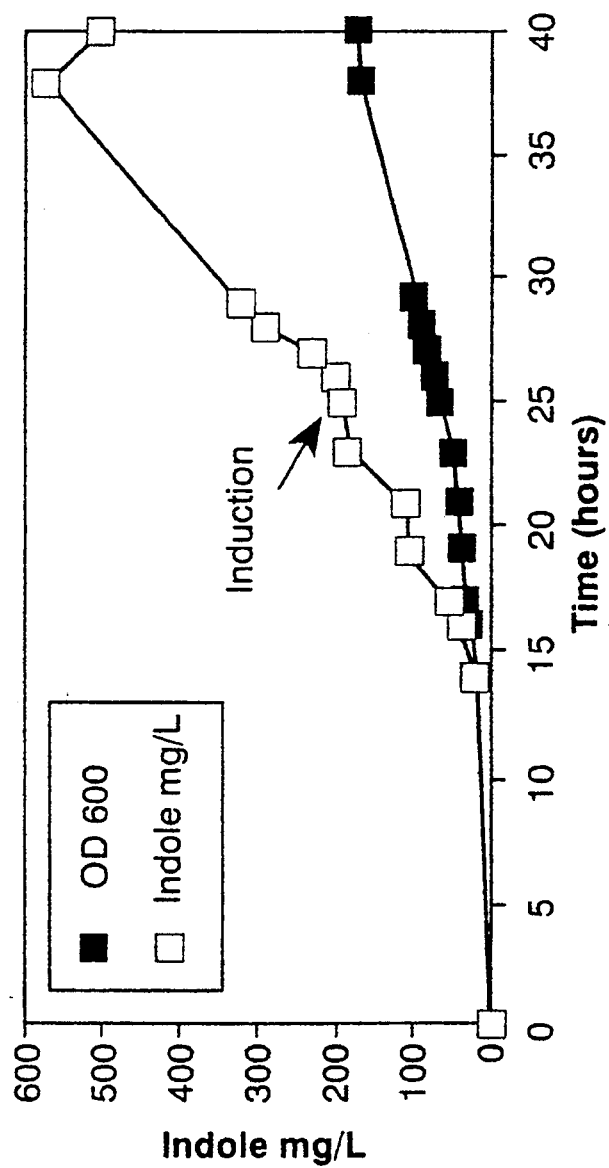
FIG. 2 graphically illustrates indole synthesis and accumulation during a 1 L fermentation of pYTrp#26.
Figure 3:
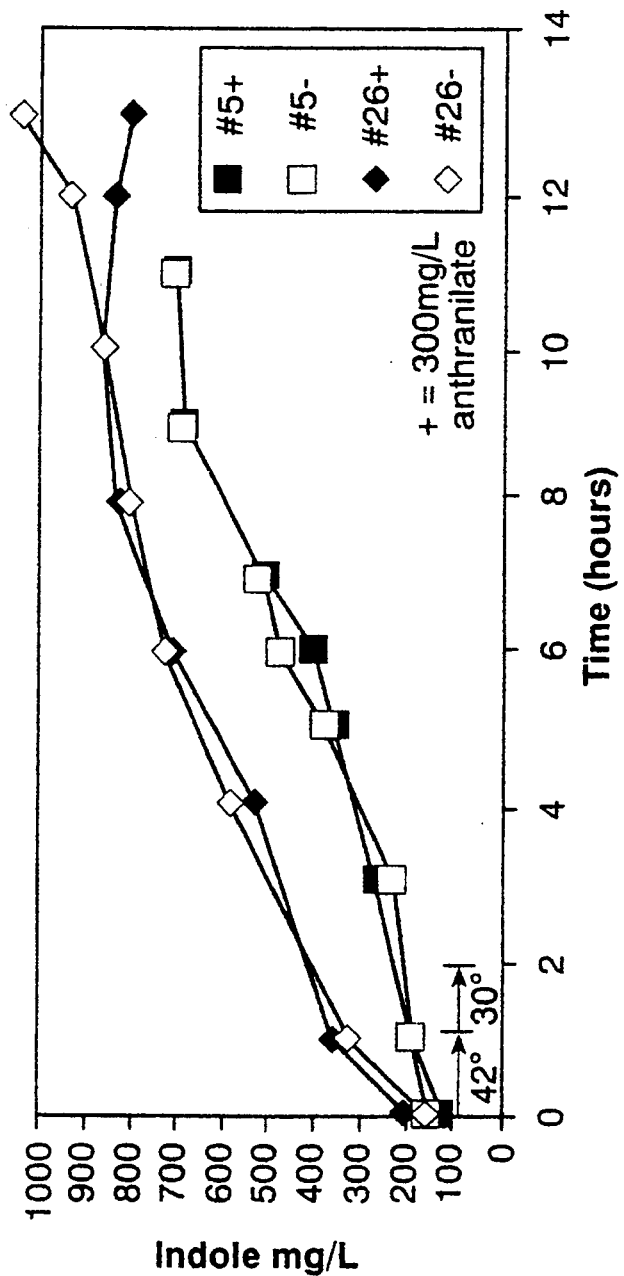
FIG. 3 graphically depicts 1 L fermentations of mutant 5 [(-□-), without anthranilate; (-■-) with 300 mg/L anthranilate] and pYTrp#26 [(-▲-), with anthranilate; (-△-), without anthranilate].

Using the above fermentation procedure, indole synthesis and accumulation was studied in pYTrp#26. The results appear in FIG. 2. In addition, mutant #5 (Table 1, supra), which harbored only a single mutation and was an intermediate indole producer in shake flasks, was also tested in the 1 L fermentor. The results of these fermentations appear in FIG. 3. As shown, pYTrp#26 produced approximately 1 g/L of indole 13 hours after trp operon expression had been induced. The ability of the cells to grow in the presence of more than 0.04–0.05% indole was also unexpected in view of the prior art. For example, see Bang et al., supra, (1983). Optimumization of fermentation conditions should enable significantly increased levels of indole production.

EXAMPLE 4

Deletion of the Trp Operon Promoter

In addition to generating specific mutations in particular genes of the trp operon designed to enable high level indole production, the indole production pathway can be further refined through the deletion of the endogenous trp promoter. Removal of this promoter should increase the efficiency of transcription of the operon from the $P_L$ promoter by eliminating the potential for repression by the trp repressor protein. In addition, removal of the trp promoter will enable improved transcriptional regulation of the trp operon employed in the practice of the present invention, namely by reducing "leakiness," as the trp promoter will no longer enable transcription initiation even while $P_L$ is repressed.

Removal of the endogenous trp promoter was accomplished by digesting pYTrp#26 with Xba I and Spe I, the Xba I site being in the plasmid's polylinker, and the Spe I site residing near the 3' end of the trp promoter. Removal of this fragment also served to remove about 400 bp of extraneous DNA 5' of the trp promoter. Also, because Xba I and Spe I leave identical 3' overhangs following digestion, removal of the intervening fragment allows the complementary "sticky ends" to come together. Thus, following agarose gel purification, the sticky ends of the linearized plasmid were allowed to anneal and the sequences ligated. In the resultant construct, both the Xba I and Spe I sites were lost. This new trp promoterless construct was designated pYTrp#26p-.

Shake flask experiments were then conducted to compare indole production in pYTrp#26p- with that in pYTrp#26. These studies indicated that pYTrp#26p- made as much or slightly more indole, and appeared to be better regulated, than pYTrp#26.

To substantiate the shake flask results and to make a comparison in a more commercially realistic setting, 1 L fermentations were conducted wherein both constructs were tested for indole production. The fermentation conditions used here were the same as those used in Example 2. These results indicated that the new promoterless trp operon construct not only produced more indole than pYTrp#26, but that the promoterless construct also exhibited improved regulation of trp operon expression. Prior to temperature induction of the $P_L$ promoter, pYTrp#26p-produced little or no indole. In contrast, the pYTrp#26 construct made about 30% of its total indole yield prior to trp operon induction. This improved regulation also appeared to increase the growth rate of pYTrp#26p- as compared to pYTrp#26.

EXAMPLE 5

Deletion of the Trp Operon Attenuator

As described in Example 4, deletion of endogenous trp regulatory regions from the trp operon utilized in this invention can result is increased indole synthesis. Beyond removal of the trp promoter, it was also possible to generate a useful modified trp operon that had the trp attenuator region deleted as well. As the attenuator can be responsible for up to 90% of the transcriptional repression of the trp operon in vivo, removal of this region was expected to enable an improved indole production rate.

To delete the trp attenuator, which was located between the trp promoter and amino terminus of the trpE gene, site directed mutagenesis was conducted wherein a unique Xho I site was added nine codons downstream from the trpE gene initiation codon. Addition of this restriction site enabled the maintenance of the wild type amino acid sequence of the trpE gene, thanks to the degenerate nature of the genetic code. Using this site, it was possible to remove the native promoter/attenuator region by digesting with Xho I and Xba I. A synthetic Xho I/Xba I linker, designed to reconstitute the nine 5' codons of the trpE gene, was then employed to complete the construct. In addition, the linker was designed to contain an efficient ribosomal binding site with consensus spacing from the $P_L$. Finally, the 3' end of the linker was engineered to contain the initial nine codons for the trpE gene, and the codons used are those "preferred" by *E. coli*. Thus, the result of this construction, designated pYTrp#26att-, was to delete the trp promoter and attenuator regions; position the trpE gene close to the $P_L$, separated by a strong ribosomal binding site; and to provide a trpE gene with "preferred"*E. coli* codons in the first nine positions of the gene's open reading frame.

This plasmid was then transformed into FM5 and compared in shake flasks to FM5 harboring pYTrp#26p-. The pYTrp#26att- harboring strain was found to grow more slowly than the strain transformed with pYTrp#26p-. However, the attenuator deficient construction enabled the production of considerably more indole.

EXAMPLE 6

Deletion of the Trp Operon Rho-dependent Terminator

In addition to removing the trp promoter, attenuator (or both) and extraneous, non-coding 5' DNA from the trp operon, it is also possible to delete DNA 3' to the trpA gene. Along these lines, a DNA sequence approximately 250 bp in length containing a rho-dependent terminator was removed from pYTrp#26 by digesting the plasmid with Ssp I and Bam HI using a 5' exonuclease activity to remove the 5' overhang left by the Bam HI digestion; purifying the linearized plasmid from the small, excised fragment; and ligating the resultant gel-purified, linearized plasmid to itself. When this construction, which still contains a rho-independent terminator 3' to the trpA gene, was compared for indole production in shake flasks against pYTrp#26, no improvement was observed. However, deletion of this extraneous DNA apparently had no deleterious effects on indole production or plasmid stability, and thus the deletion may be useful in that the indole-producing trp operon was further streamlined through the elimination of extraneous non-coding DNA.

EXAMPLE 7

Translocated Host Strains

Because biosynthetic indigo production from glucose requires both an enzymatic pathway having the ability to produce intracellular indole and an enzymatic pathway possessing the ability to convert that indole to indoxyl, it is necessary that the strain which produces indigo harbor both pathways. One way in which this may be accomplished is to integrate either of the two pathways (trp or NDO) into the chromosome of an appropriate host bacterium and, after successful integration, transform the host with the other pathway such that it will be maintained extrachromosomally.

In one such method, the indole-generating trp operon was excised from pYTrp#26 as an Aat I to Bam HI fragment, purified through an agarose gel and then inserted into the translocation vector pCFM2202, which contains a DNA fragment from a pBR322 construct comprising Tn5 transposase gene and including the IS50L insertion sequence essential for chromosomal integration on either side of the DNA to be integrated [Sasakawa et al., (1982) *Proc. Natl. Acad. Sci., USA*, vol. 79, pp. 7450–7454]. The translocation vector provides for selection using the antibiotic tetracycline. In addition, it directs the integration of the desired, inserted DNA sequence, here the modified trp operon, in conjunction with the structural gene for the $cI_{857}$ regulatory element, which itself is under the control of a low-level constitutive promoter. Following assembly, the trp operon integration plasmid was designated pCFM2202Trp and was transformed into *E. coli* strain FM5. Following transformation, the strain was redesignated DM2.

After transformation, several transformants were selected and passaged for 13 generations in non-selective media in order to "cure" the cells of the plasmid. Subsequent to passaging, plasmid deficient cells containing the a trp operon were identified by colony hybridization [Manniatas et al., supra] using an oligonucleotide probe specific for the #26 trpB gene mutation. Several isolates were examined for their indole producing ability. The translocated strain designated DM2#26 was found to be the most proficient indole producer of the translocatants. DM2#26 was then compared against FM5 transformed with pYTrp#26. Upon induction, the translocated strain was found to produce approximately 20% more indole than its plasmid bearing sibling, although the integrant grew more slowly than the strain harboring the extrachromosomal element. Finally, in an effort to assess whether or not DM2#26 could produce indigo if presented with an appropriate indole to indoxyl conversion mechanism, it was transformed with pFd911ABC. A resultant transformant, harboring the integrated modified trp operon and a plasmid-borne NDO pathway, was observed to make low levels of indigo in shake flasks.

While the present invention has been described in terms of preferred embodiments, it is understood that variations and modifications will occur to those skilled in the art in light of the above description. Therefore, it is intended that the appended claims cover all such variations which come within the scope of the invention as claimed.

---

What is claimed is:

1. A purified and isolated DNA molecule encoding a non-naturally occurring tryptophan synthase beta-subunit polypeptide, the DNA molecule comprising substitution of two codons, a first substitution comprising a codon encoding an amino acid residue selected from the group consisting of Pro, Val, Ile, Leu, and Ala at the codon corresponding to amino acid position trpB$^{379}$ and a second substitution comprising a codon encoding an amino acid residue selected from the group consisting of Asn, Gly, and Met at the codon corresponding to amino acid oisition trpB$^{382}$ which, when incorporated into tryptophan synthase, results in enhanced indole accumulation in a recombinant microorganismic host relative to a tryptophan synthase beta-subunit having Asn instead of Lys at amino acid position 382.

2. A DNA molecule according to claim 1 wherein the substituted codon codes from Pro at the codon corresponding to amino acid position trpB$^{379}$.

3. A DNA molecule according to claim 1 wherein the substituted codon codes forMet at the codon corresponding to amino acid position trpB$^{382}$.

4. A DNA molecule according to claim 1 wherein the substituted codon corresponding to amino acid position trpB$^{379}$ codes for Pro and the substituted codon corresponding to amino acid position trpB$^{382}$ codes for Met.

5. A DNA molecule according to claim 1 further comprising the DNA sequences for one or more genes selected from the group consisting of trpE, trpD, trpC, and trpA.

6. A purified and isolated DNA molecule encoding a non-naturally occurring trytophan synthase beta-subunit polypeptide, the DNA molecule comprising substitution of two codons, a first substitution comprising a codon encoding an amino acid residue selected from the group consisting of Pro, Valm Ile, Leu, and Ala at the codon corresponding to amino acid position trpB$^{379}$ and a second substitution comprising a codon encoding an amino acid residue selected from the group consisting of Asn, Gly, and Met at the codon corresponding to amino acid position trpB$^{382}$ which, when incorporated into tryptophan synthase, results in decreased formation of tryptophan from indole and serine in a recombinant microorganismic host relative to a tryptophan synthase beta-subunit having Asn instead of Lys at amino acid position 382.

7. A procaryotic or eucaryotic host cell stably transformed or transfected with a DNA molecule according to claim 1 in a manner allowing the host cell to express the tryptophan synthase under appropriate conditions.

8. A procaryotic host cell according to claim 7 that is *Escherichia coli*.

9. A biologically functional plasmid or viral DNA vector including a DNA molecule according to claim 1.

10. A procaryotic or eucaryotic host cell stably transformed or transfected with a DNA vector according to claim 9 in a manner allowing the host cell to express the tryptophan synthase under appropriate conditions.

11. A procaryotic host cell according to claim 10 that is *Escherichia coli*.

12. A method for the biosynthesis of indole in a selected host microorganism comprising the steps:
   a) stably transforming or transfecting the microorganism with a purified and isolated DNA molecule encoding a non-naturally occurring tryptophan synthase beta-subunit polypeptide, the DNA molecule comprising substitution of two codons, a first substitution comprising a codon encoding an amino acid residue selected from the group consisting of Pro, Val, Ile, Leu, and Ala at the codon corresponding to amino acid position trpB$^{379}$ and a second substitution comprising a codon encoding an amino acid residue selected from the group consisting of Asn, Gly, and Met at the codon corresponding to amino acid position trpB$^{382}$ which results in enhanced indole accumulation relative to a tryptophan synthase betasubunit having Asn instead of Lys at amino acid position 382; and
   b) cultivating the transformed or transfected microorganism of part (a) under conditions producing intracellular indole.

13. A DNA molecule according to claim 12 wherein the substituted codon corresponding to amino acid position trpB$^{379}$ codes for Pro and the substituted codon corresponding to amino acid position trpB$^{382}$ codes for Met.

14. A method according to claim 12 wherein the DNA molecule is integrated into the chromosome of the host microorganism.

15. A method according to claim 12 wherein the DNA molecule is contained in an extrachromosomal element capable of directing the expression of genes included in the DNA molecule under appropriate conditions.

16. A method for the biosynthesis of indigo in a selected host microorganism comprising the steps:
   a) stably transforming or transfecting the microorganism with a purified and isolated DNA molecule encoding a non-naturally with tryptophan synthase beta-subunit polypeptide, the DNA molecule comprising substitution of two codons, a first substitution comprising a codon encoding an amino acid residue selected from the group consisting of Pro, Val, Ile, Leu, and Ala at the codon corresponding to amino acid position trpB$^{379}$ and a second substitution comprising a codon encoding an amino acid residue selected from the group consisting of Asn, Gly, and Met at the codon corresponding to amino acid position trpB$^{382}$ which results in enchanced indole accumulation relative to a tryptophan synthase beta-subunit having Asn instead of Lys at amino acid position 382; and
   b) stably transforming or transfecting the microorganism with a DNA molecule encoding aromatic dioxygenase enzyme capable of converting indole to indoxyl;
   c) cultivating the microorganism under conditions facilitating expression of polypeptides encoded by the DNA molecules of parts (a) and (b) such that expression of such polypeptides enables intracellular indole accumulation and conversion of indole to indoxyl;
   d) oxidizing indoxyl to indigo; and
   e) recovering the indigo so produced.

17. A DNA molecule according to claim 16 wherein the substituted codon corresponding to amino acid position trpB$^{379}$ codes for Pro and the substituted codon corresponding to amino acid position trpB$^{382}$ codes for Met.

18. A method according to claim 16 wherein the DNA molecule of part (a) is integrated into the chromosome of the host microorganism.

19. A method according to claim 16 wherein the DNA molecule of part (a) is contained in an extrachromosomal element capable of directing the expression of genes included in the DNA molecule under appropriate conditions.

20. A method according to claim 16 wherein the DNA molecule encoding an aromatic dioxygenase enzyme is integrated into the chromosome of the host microorganism.

21. A method according to claim 16 wherein the DNA molecule encoding an aromatic dioxygenase enzyme is harbored in an extrachromosomal element capable of directing the expression of genes included in the DNA molecule under appropriate conditions.

22. A method according to claim 16 wherein the DNA molecules of parts (a) and (b) are harbored in the same extrachromosomal element, the extrachromosomal element being capable of directing the expression of genes encoded by the DNA molecules under appropriate conditions.

* * * * *